United States Patent [19]

McDonough

[11] Patent Number: 5,843,131
[45] Date of Patent: Dec. 1, 1998

[54] HEART DEFIBRILLATOR EITH E-PAC CHASSIS

[75] Inventor: William J. McDonough, McMinnville, Oreg.

[73] Assignee: Hewlett-Packard Company, Palo Alto, Calif.

[21] Appl. No.: 889,662

[22] Filed: Jul. 8, 1997

Related U.S. Application Data

[62] Division of Ser. No. 441,899, May 16, 1995, Pat. No. 5,691,881.

[51] Int. Cl.$^6$ .................................................. A61N 1/39
[52] U.S. Cl. .............................. 607/5; 361/682; D24/168
[58] Field of Search ................................ 607/5; 361/682; D24/168

[56] References Cited

U.S. PATENT DOCUMENTS

| | | |
|---|---|---|
| D. 253,610 | 12/1979 | Smith et al. . |
| 5,464,428 | 11/1995 | Hill . |
| 5,607,454 | 3/1997 | Cameron et al. ........................... 607/5 |

FOREIGN PATENT DOCUMENTS

| | | | |
|---|---|---|---|
| 167 122 | 1/1986 | European Pat. Off. ......... | A61N 1/39 |
| 546 211 | 6/1993 | European Pat. Off. ......... | H05K 7/14 |

*Primary Examiner*—William E. Kamm
*Assistant Examiner*—Carl H. Layno

[57] ABSTRACT

An electronic device has a chassis configured to hold multiple electronic components in a predefined three-dimensional arrangement whereby some of the electronic components are positioned elevationally above, and overlapping, other electronic components. Each electronic component has an external dimension which falls within a tolerance range between a lower acceptable tolerance limit and an upper acceptable tolerance limit. The chassis has form fitting recesses to receive and hold the electronic components. Each chassis recess is undersized relative to the lower acceptable tolerance limit for the external dimension of an associated electronic component, but the chassis has effective compliant qualities to receive and hold an electronic component even if it has an external dimension at the upper acceptable tolerance limit. The electronic components are interconnected by conductive cables. The chassis has patterned cable channels formed therein to hold and guide the cables through predefined locations within the electronic device between the electronic components.

10 Claims, 7 Drawing Sheets

HEART DEFIBRILLATOR EITH E-PAC CHASSIS

RELATED APPLICATIONS

This is a divisional of U.S. patent application Ser. No. 08/441,899, filed May 16, 1995, which is now U.S. Pat. No. 5,691,881.

TECHNICAL FIELD

This invention relates to an electronic device having a chassis for mounting multiple electronic components. Particularly, this invention relates to an E-PAC (electronic packaging assembly concept) chassis for a heart defibrillator system which provides spatial arrangement of electronic components, such as a CRT display monitor and a capacitor, as well as uniform cable organization.

BACKGROUND OF THE INVENTION

Figure 1:
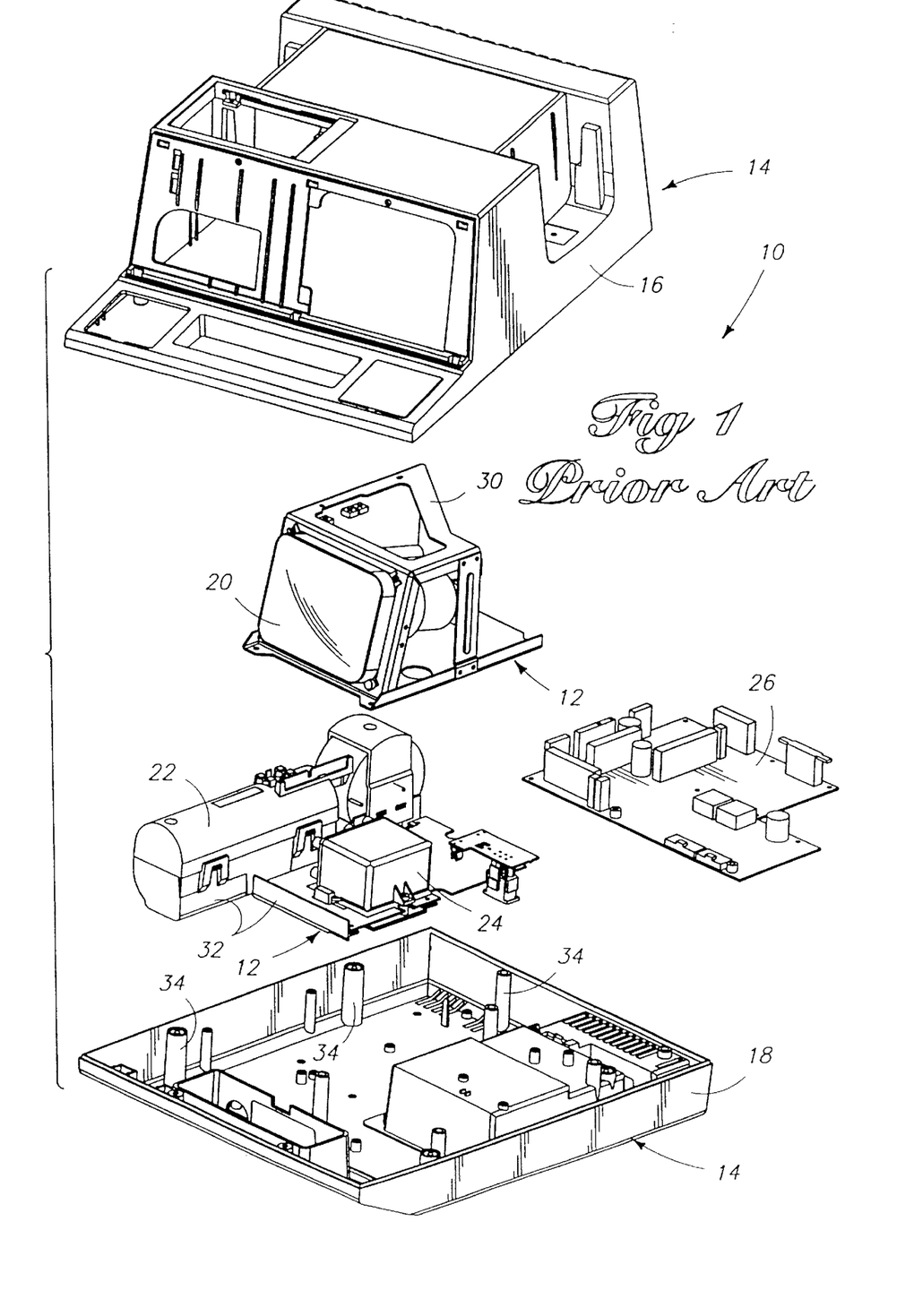
FIG. 1 is an exploded view of a conventional heart defibrillator system having a metal chassis.

A chassis for an electronic device typically includes a plastic or metal framework mounted within an external housing. Various electronic components that make up the electronic device are attached to the framework. FIG. 1 shows a conventional chassis 12 for a heart defibrillator system 10. Chassis 12 holds the electronic components within an external housing 14, which includes an upper housing member 16 and a lower housing member 18. The primary electronic components of defibrillator system 10 are a CRT display monitor 20, a capacitor assembly 22, and a relay 24 which isolates a human patient from defibrillating pulse generation circuitry. System 10 also has a circuit board 26.

Chassis 12 includes an internal monitor frame 30 which is assembled from many individual brackets. CRT display monitor 20 is mounted to monitor frame 30. Chassis 12 also includes capacitor frame 32 that supports capacitor assembly 22. Monitor frame 30 and capacitor frame 32 are mounted to housing 14 via screws, bolts, or other fastening elements. Lower housing member 18 is formed with bosses 34 to maintain the appropriate spacing and orientation of the frames and circuit boards at predefined locations within the housing when the defibrillator system is assembled.

Each of the frame pieces (e.g., monitor frame 30 or capacitor frame 32) are formed of metal or plastic. For a metal chassis, metal sheets are stamped or bent to a desired shape and then treated using a galvanizing process. For plastic pieces, the frame parts are injection molded into the appropriate shape. The frame pieces are then assembled using screws, bolts, welding, rivets, glue, or other fastening techniques to form the chassis.

Once the chassis is assembled, the electronic components are mounted to it. For instance, CRT display monitor 20 is positioned and secured to monitor frame 30 via four screws at the corners of the monitor. Likewise, the capacitor elements are assembled and mounted to frame 32. Apart from structural support, the chassis also lends the dimensional organization of the electronic components within a three-dimensional space allocated by housing 14.

To ensure that the electronic components will all fit in the housing space, the external dimensions of each component must comply with preset tolerance ranges. These tolerance ranges account for inherent imperfections in the manufacturing process and dimension variability that tends to occur from one manufacturer to another. Some components have larger tolerance ranges than others. For instance, the CRT display monitor has a relatively large tolerance range due in part to the inaccuracies associated with molding the glass used in the monitor.

Conventional chassis are designed to accommodate electronic components that fall within the tolerance range. Typically, the chassis is configured to accommodate the largest sized components, while providing some adjustability to handle the smallest sized components. To accommodate varying external dimensions of CRT display monitor 20, for example, monitor 20 is constructed with four U-shaped prongs which are located at the four corners of the glass monitor and extend radially outward to be securely mounted to monitor frame 30 via screws. The U-shaped prongs or "ears" are elongated a sufficient length to account for size variances. As a result, the CRT display monitor can be mounted to frame 30 regardless of whether the CRT glass is at the smallest extreme or largest extreme of the established monitor tolerance range. Apart from the CRT monitor, the conventional chassis and fastening components all have built in error margins which enable the assembly of imperfect and inconsistently sized electronic components.

As part of the natural product evolution, it is typically a design goal to make electronic devices smaller and more compact. One way to achieve this goal is to make the components themselves smaller. Another common way to accomplish the goal is to organize the components in a space-savings arrangement. However, by accounting for the largest size tolerances in the various components, the overall chassis necessarily has buffer margins to ensure that all components will fit in the housing. A designer is often hard pressed to find a practical way to reduce the size of the chassis, and hence the overall device, while still accommodating the various tolerance ranges.

One aspect of this invention is to provide a chassis that organizes the electronic components in a compact, three-dimensional space without sacrificing the practical need to accommodate various tolerance ranges of the electronic components.

After the components are mounted to the chassis, the components are interconnected with some form of conductive cabling, such as wires, busses, or ribbon cabling. Standard cabling practice is to gather groups of cables and join them with fasteners (such as wire clips) to form cable bundles that are manually arranged into some convenient, out-of-the-way vacant portion of the housing space. Where ribbon cabling is used, the assembly person simply arranges the cable itself if a more sophisticated cable management is desired, it is common to position internal mold ed support parts or hooks at prescribed locations. The cable is fastened to the hooks, point-by-point, grand the intermediate portion between adjacent hooks is left dangling. The-free portion of the cable has a tendency to move around within the housing. In some electronic devices, such as a heart defibrillator system, the uncertainty of cable location can undesirably cause excessive interference, such as radio frequency interference (RFI). Different geometric locations of the internal cables result in different loop areas in the emissions of radio frequencies. These differences have an effect on the variability of the RFI emissions and may result in greater margins than that required for regulatory approvals.

Another aspect of this invention is to provide an enhanced technique for managing cables within an electronic device.

The overall assembly process is time-consuming. One reason is that there are a fairly large number of parts counting the chassis—which includes individual frame pieces, screws, nuts, bolts, washers, spacers, etc.—and the components themselves. Another reason is that the assembly process requires time-involved assembly of the chassis, followed by the assembly of each component to the chassis. The process is not conducive to automation, but instead is practically limited to hand or manual assembly. Apart from assembly, there is an additional review time to ensure that each component is properly and securely fastened to the chassis. If a component is improperly mounted, excessive vibration might result, potentially causing damage to that component and those components around it. The prolonged assembly time drives up costs, as does the number of individual assembly parts.

Another aspect of this invention is to provide an electronic device that is easy to assemble, conducive to automated assembly, and is less expensive to produce and assemble by virtue of elimination of many assembly parts.

To eliminate the number of parts associated with conventional metal or plastic frames, a new packaging process known as E-PAC (electronic packaging assembly concept) has recently been pioneered and introduced in some products by Hewlett-Packard Company. E-PAC is a technique where the electronic components are first placed in a protective frame-like foam material, and then the foam material is inserted into the housing. The foam material is a bumper grade expanded polypropylene (EPP) which is molded into form-fitting pieces that hold the electronic components.

Is The general use of E-PAC as a chassis for an electronic device is described in a European Patent Application EP 0 546 211 A1. The E-PAC chassis replaces the conventional metal framework. The European Application defines a two piece chassis used to hold electronic components in a common computer workstation. Most of the components are held in a planer arrangement between the two pieces. The use of E-PAC as a chassis is a significant advance because it eliminates many component parts while still providing a secure, vibration and noise reducing framework within which components are mounted. The E-PAC significantly reduces assembly time and enables automated assembly. However, further enhancements and modifications were not contemplated by the inventors of EP 0546211 A1 that, if made, could result in additional benefits.

SUMMARY OF THE INVENTION

This invention pertains to an electronic device with an improved chassis. The electronic device includes first and second electronic components which are interfaced via a conductive cable. Each electronic component has an external dimension which falls within a tolerance range between a lower acceptable tolerance limit and an upper acceptable tolerance limit. The electronic device also includes a chassis having form-fitting recesses configured to receive and hold the first and second electronic components a spaced distance apart. Preferably, the chassis is an E-PAC (electronic packaging assembly concept) chassis that is formed of expanded polypropylene. Each chassis recess is undersized relative to the lower acceptable tolerance limit for the external dimension of its associated electronic component. However, the chassis has effective compliant qualities to receive and hold the electronic components even in the event that the external dimensions of the electronic components are at their upper acceptable tolerance limits. In this manner, the chassis accounts for size variations in the electronic components.

The chassis holds the first and second electronic components in a predefined three-dimensional arrangement. For instance, the first electronic component can be positioned elevationally above, and overlapping, the second electronic component. In one implementation of a heart defibrillator system, the chassis supports a CRT display monitor along one longitudinal axis and supports a capacitor elevationally above, and overlying, the CRT display monitor along a second longitudinal axis that is perpendicular to the first axis. Accordingly, the chassis organizes the electronic components (in this case, the CRT monitor and capacitor) in a compact, three-dimensional space while accommodating the tolerance ranges of the electronic components.

A cable channel is formed in the chassis to hold and guide the cable through predefined locations within the electronic device between the first and second electronic components. Rather than bundling the cable wires using clips or hooks, the cable wires are inserted into the pre-formed cable channel and held therein by friction. The pre-formed channel provides uniformity in cable placement within the electronic device which thereby reduces the variability of RFI emissions from one manufactured device to the next.

DETAILED DESCRIPTION OF THE PREFERRED EMBODIMENT

Figure 2:
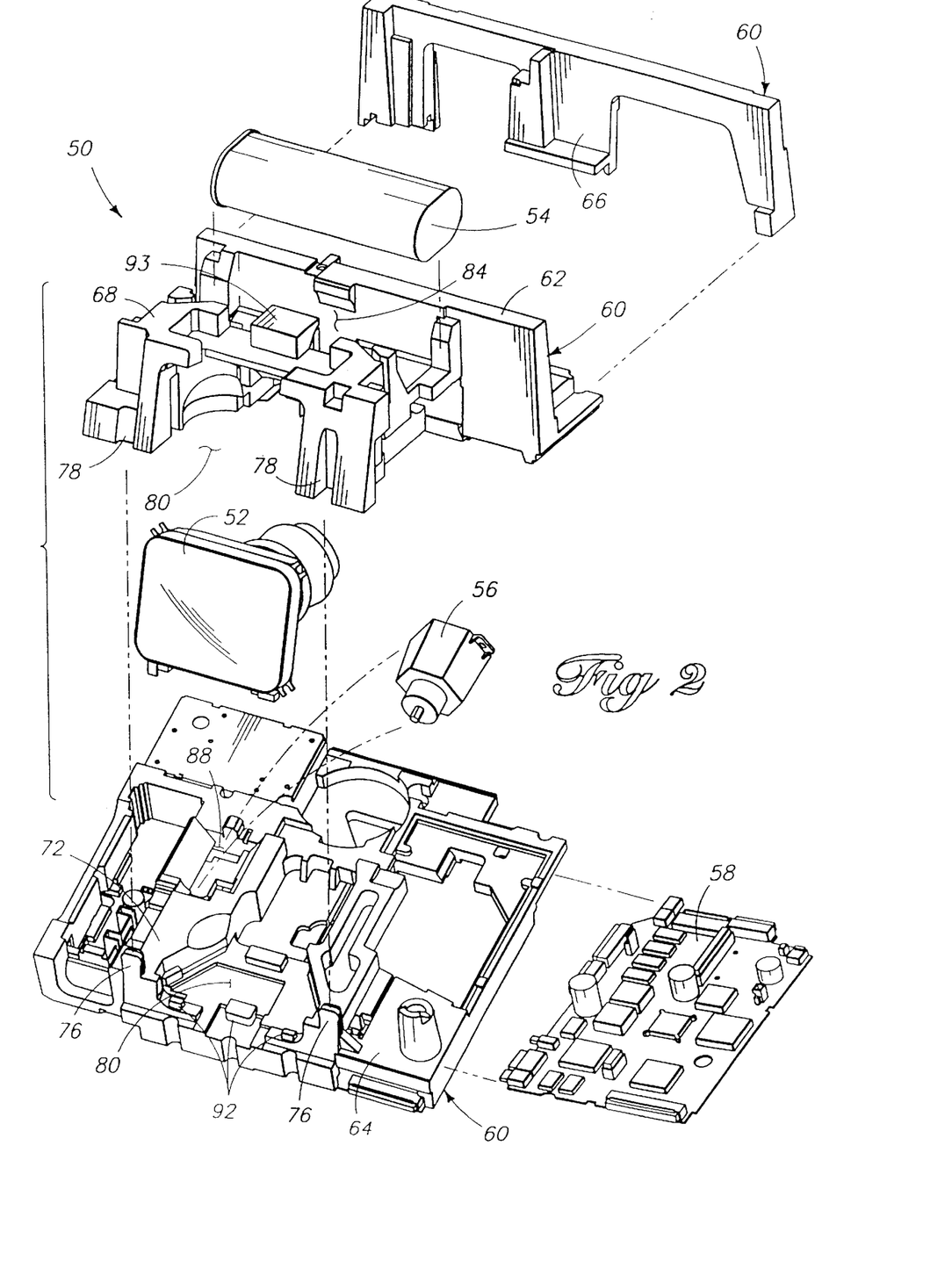
FIG. 2 is an exploded view of a heart defibrillator system having a chassis according to the preferred embodiment of this invention.

FIG. 2 shows an electronic device 50 constructed according to the preferred embodiment of this invention. For purposes of discussion, electronic device 50 is shown in an exemplary implementation as a heart defibrillator system. The primary electronic components of the defibrillator system are a CRT display monitor 52, a capacitor 54, and a relay 56. The defibrillator system also includes a control circuit board 58. The operation of the defibrillator system and the function of these components are conventional and are not described in detail herein.

Figure 4:
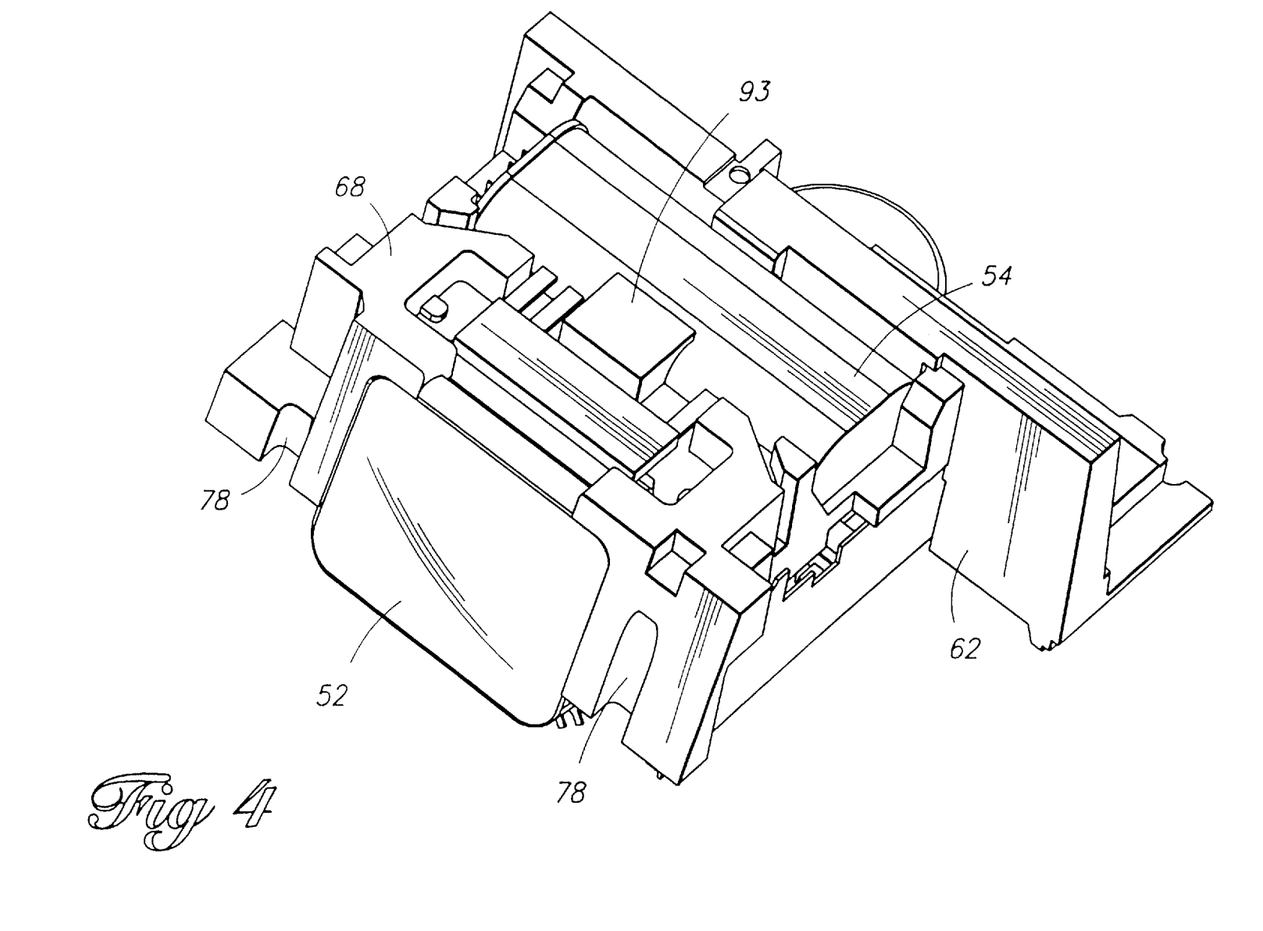
FIG. 4 is a top isometric view of an upper member of the chassis of FIG. 2.

Electronic device 50 has a chassis 60 which holds the electronic components within an external housing (not shown, but similar to housing 14 shown in FIG. 1). Chassis 60 has three members: a first or upper member 62, a second or lower member 64, and a third or rear member 66. The upper member 62 has a top outer surface 68, which is also shown in FIG. 4, and an inner surface 70, which is shown more clearly in FIG. 5. Similarly, the chassis lower member 64 has an inner surface 72, which is shown in FIG. 6, and a bottom outer surface 74, which is shown more clearly in FIG. 7.

When assembled, the inner surfaces 70 and 72 are juxtaposed in facing relationship with one another. An orientation coupling assembly is provided to orient and align the upper and lower members for proper assembly. In the illustrated embodiment, the orientation coupling assembly comprises projections 76 formed on lower member 64 and corresponding, complimentary slots or grooves 78 formed in upper member 62. During assembly, projections 76 are aligned with corresponding grooves 78 to ensure proper orientation and alignment of the upper and lower chassis members.

Figure 3:
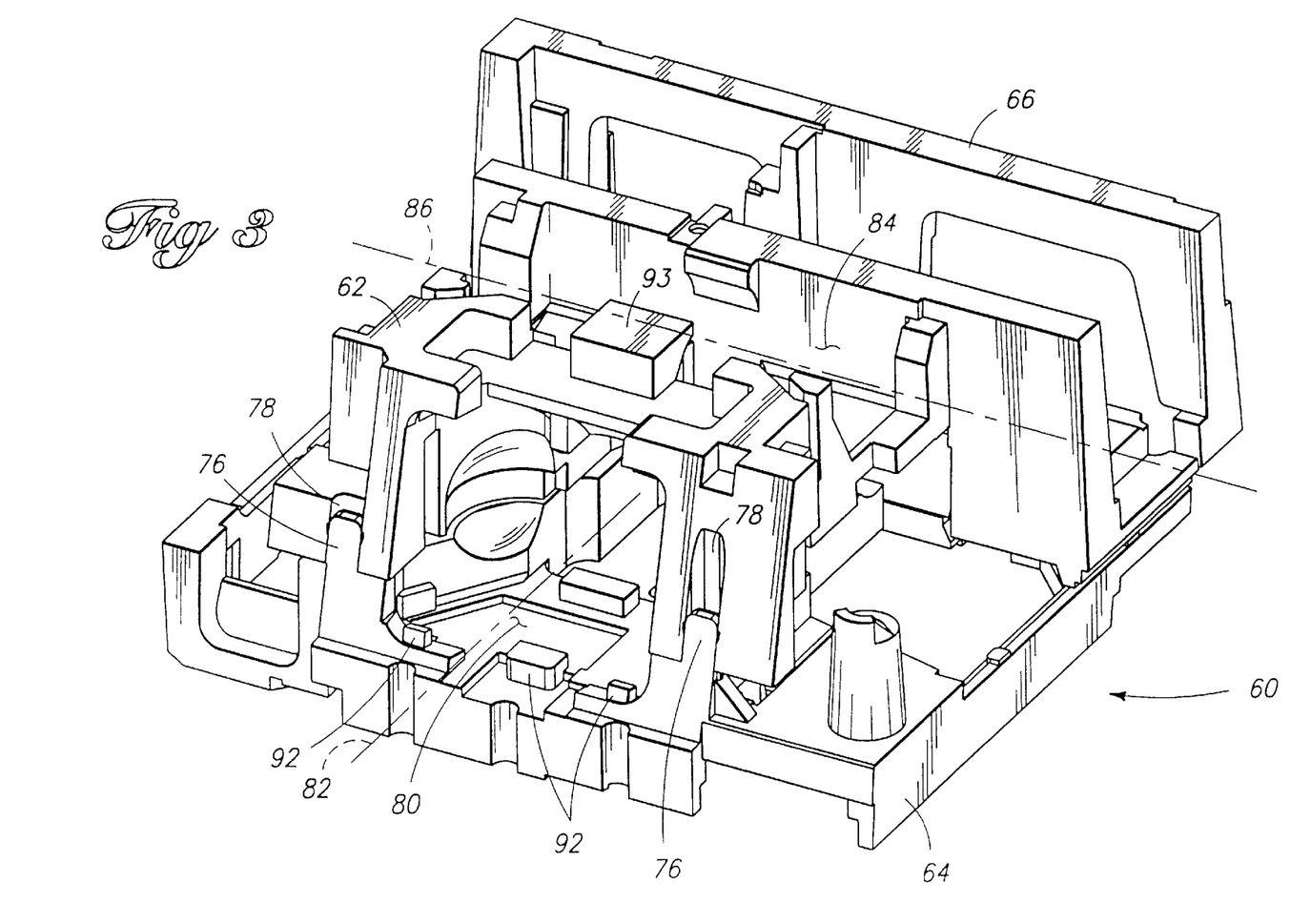
FIG. 3 is an isometric view of the chassis of FIG. 2 in an assembled state, and without the electronic components.

FIG. 3 shows chassis 60 in an assembled state, and without the electronic components for purposes of illustration. The three chassis members form a frame unit having form-fitting recesses configured to receive and hold associated electronic components. For instance, chassis 60 includes a monitor cavity or recess 80 formed partly in the inner surface 70 of upper member 62 and partly in the inner surface 72 of lower member 64. The monitor recess 80 extends along a first longitudinal axis 82. Chassis 60 further includes a capacitor recess 84 formed in the outer surface 68 of upper member 62. Capacitor recess 84 is aligned along a second longitudinal axis 86 that is substantially perpendicular to the first longitudinal axis 82 of monitor recess 80. As shown in FIGS. 2, 5, 6, and 7, chassis 60 also includes a relay recess 88 formed partly in both inner surfaces of upper and lower members 62 and 64. Relay recess 88 is sized to receive and hold relay 56. Chassis 60 further includes a circuit board recess 90 formed in the bottom outer surface 74 of lower member 64 to hold circuit board 58.

Each electronic component has an external dimension which falls within a tolerance range between a lower acceptable tolerance limit and an upper acceptable tolerance limit. As noted in the Background section of this disclosure, some components have larger tolerance ranges than others. For instance, the CRT display monitor and capacitor have a relatively large tolerance range due in part to manufacturing inaccuracies. The recesses formed to hold these components are therefore purposely undersized relative to the lower acceptable tolerance limit for the external dimension of the associated electronic component. For example, monitor recess 80 is formed smaller than the expected smallest external dimension of the CRT display monitor to ensure that a comparatively small CRT display monitor is adequately held in the chassis. However, the chassis has effective compliant qualities to receive and hold an electronic component even in the event that the external dimension of that electronic component is at the upper acceptable tolerance limit. Thus, even if the CRT display monitor is at the large extreme of its tolerance range for external dimensions, the chassis frame unit will accommodate the large size monitor. In this manner, the chassis accounts for size variations in the electronic components.

The chassis is preferably an E-PAC (electronic packaging assembly concept) chassis that is formed of "bumper grade" expanded polypropylene (EPP). The three chassis members are formed using injection molding techniques. More specifically, an EPP-based chassis is produced by first creating foamed up polypropylene granules according to a known method to produce polypropylene beads. The granules contain carbon which ensures that the final plastic material has an electric conductivity sufficient to avoid electrostatic charging of the chassis. Then, the beads are blown with a pressure of about 4 bar into a desired form of a chassis member. This step leads to a volume reduction.

In a subsequent step, vacuum is applied to increase the volume and the beads assume the shape of the form. Next, hot water vapor of about 180° C. is blown in, causing coalescence of the beads at their surfaces (i.e., cross-linkage). After that, the form is opened and the foam part is removed. Finally, the part is tempered. The process for forming an EPP-based chassis is described in more detail in European Patent Application EP 0 546 211 A1, which is assigned to Hewlett-Packard Company.

Expanded polypropylene has several advantageous properties which make it suitable as a plastic material for a chassis design of this invention. For example, expanded polypropylene has high-dimensional stability, and yet is resilient and energy absorbent. This ensures a shock-absorbing mounting of the electronic components in the chassis. For instance, the custom molded pocket or recess for relay 56 that is formed in the polypropylene chassis allows for shock and vibration absorption around the electronically delicate relay.

The deformability or resilience of the plastic material can be influenced by the density of the material. In an example chassis, the density of the polypropylene is in a range of about 60 to 80 grams/liter which provides both dimensional stability and a good shock-absorbing effect. A broader density range of 25–80 grams/liter may also be used for certain applications. By varying the density, the hardness and shock-absorbing characteristics of the expanded polypropylene can be adjusted to the specific application. As density decreases, the material becomes softer, resulting in a better shock-absorbing quality. Another advantage of polypropylene is its temperature stability which is important when the components carried by the chassis generate a large amount of heat. Another advantage of polypropylene is that it can be completely recycled.

Although most preferred, expanded polypropylene is not the only possible plastic material having advantageous properties which make it suitable for use as a chassis according to this invention. Other plastic materials with dimensional stability and a certain resilience can also be used as the chassis material. The plastic materials ought to be moldable to form the chassis shape and contour. Alternative materials are polyurethane or polyethylene, although these materials are not quite as satisfactory as polypropylene in all respects.

Figure 5:
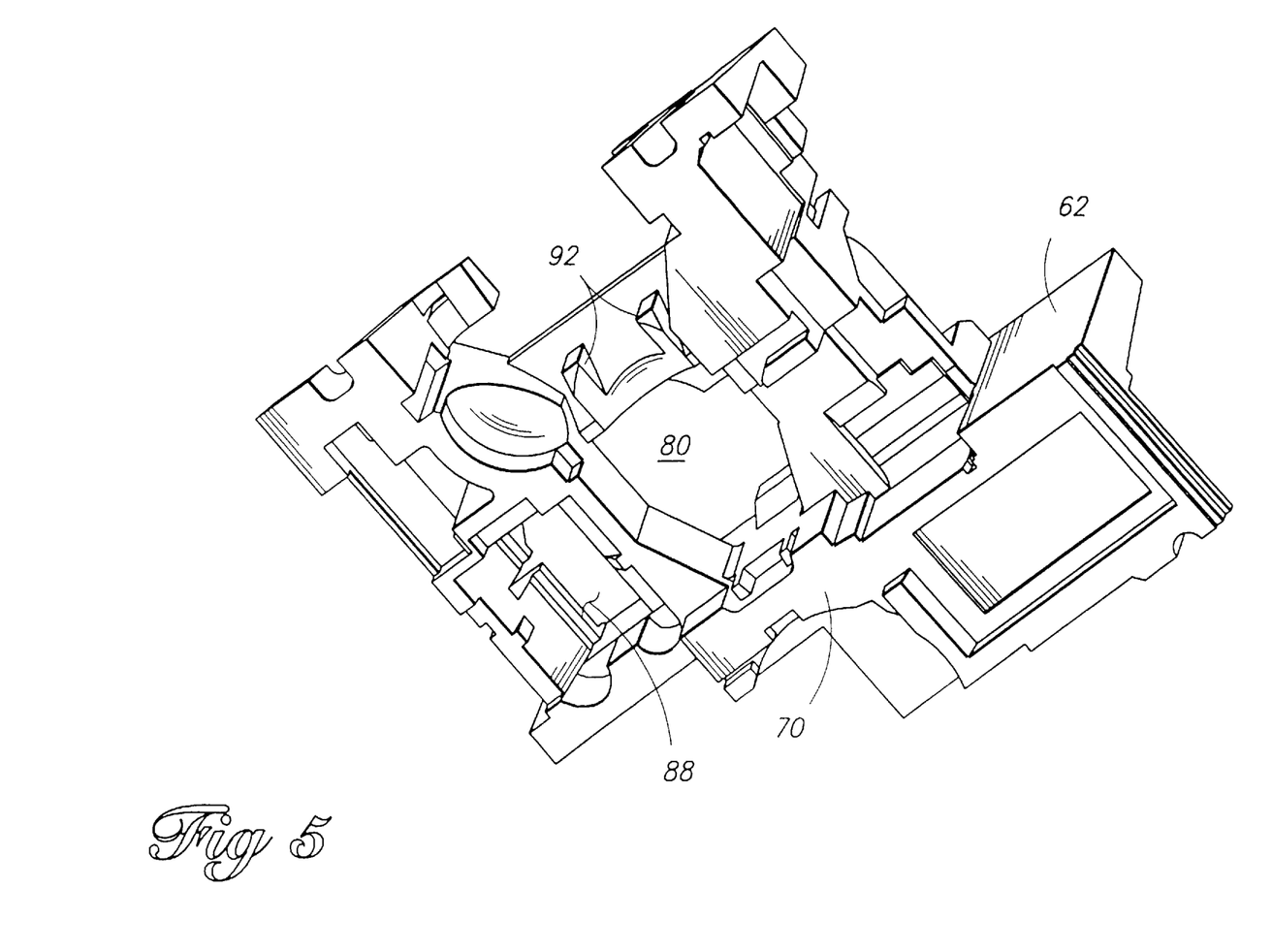
FIG. 5 is a bottom isometric view of the upper member of the chassis of FIG. 2.
Figure 6:
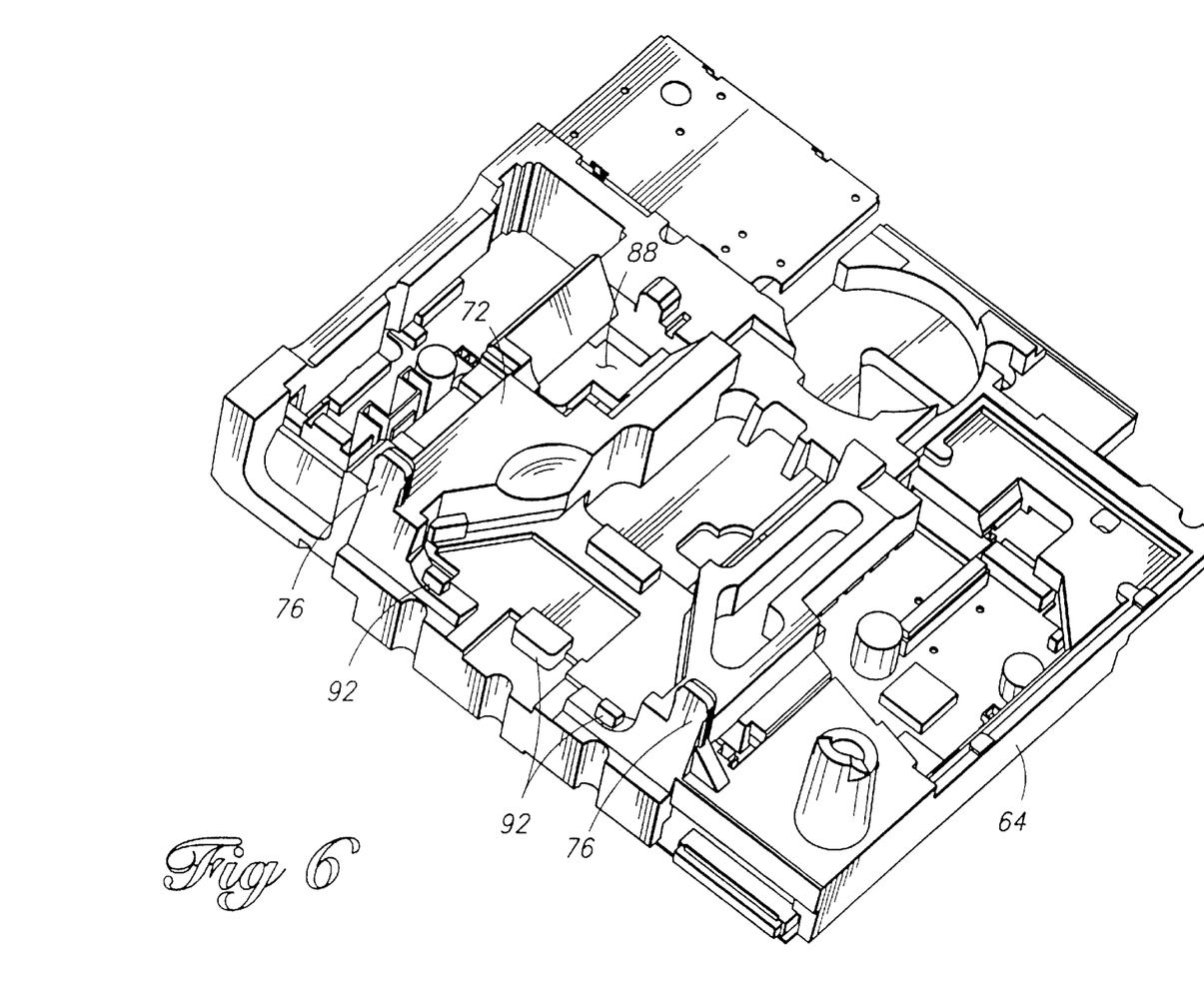
FIG. 6 is a top isometric view of a lower member of the chassis of FIG. 2.

With reference to FIGS. 2, 3, and 5, chassis 60 includes deformable ribs 92 about monitor recess 80. Ribs 92 are thin, more compliant projections which deform under pressure from the CRT display monitor 52 to orient and hold the monitor in the appropriate location within monitor recess 80. The deformable ribs 92 adjust to the tolerance differences of the CRT display monitor. Upper member 62 also has a cantilevered latch element 93 that projects out above the capacitor recess 84. During assembly, capacitor 54 is inserted down into the recess and snap element 93 bends to permit passage of the capacitor. Once the capacitor is moved past element 93 and positioned in the recess, the latch element 93 returns to its prebent position to operatively hold the capacitor in its recess 84.

Chassis 60 holds the electronic components in a pre-defined three-dimensional arrangement within a three-dimensional housing space, which has a depth, a width, and a height. The chassis both defines the location of the components as well as provides the desired spacing between adjacent components. Some of the electronic components overlap with others within the three-dimensional space. For instance, as shown in FIGS. 2 and 3, capacitor 54 is held within recess 84 elevationally above, and overlying, CRT display monitor 52 which is held within monitor recess 80. The chassis has separating elements interleaved between the capacitor 54 and CRT display monitor 52 to provide the appropriate spacing therebetween.

As a result, the chassis of this invention organizes the electronic components, such as the CRT monitor and capacitor in a compact, three-dimensional space while accommodating the tolerance ranges of the electronic components. The three-dimensional organization afforded by the chassis is advantageous over prior art metal frameworks. For instance, in a prior art heart defibrillator system, the capacitor is mounted directly on a special circuit board assembly to the side of the CRT display monitor (rather than above it) because this arrangement is most convenient for the metal chassis framework. Moreover, the internal metal support elements, as well as screws, clips, bosses, spacers, and other assembly parts, are eliminated and replaced by pre-formed pockets.

Figure 7:
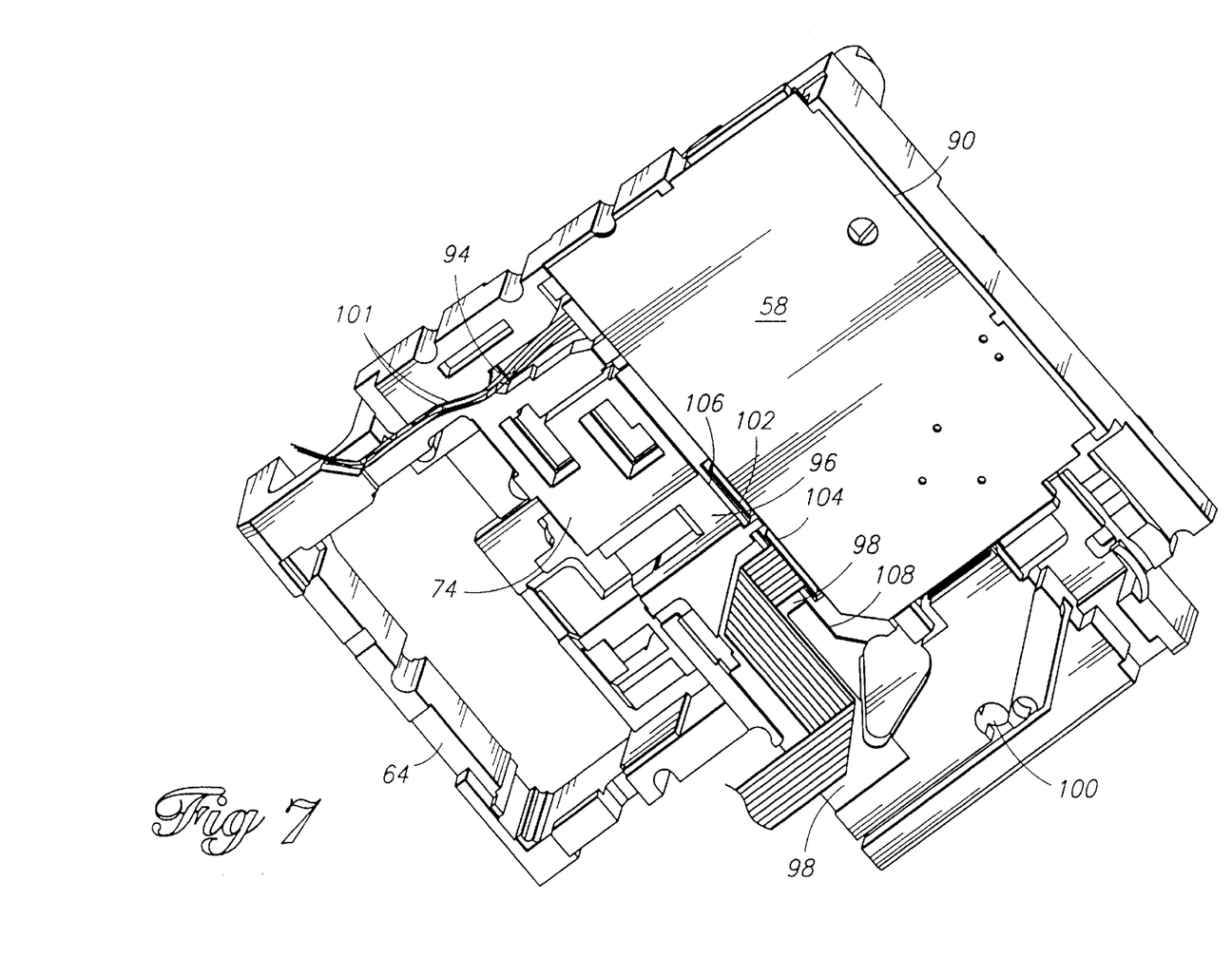
FIG. 7 is a bottom isometric view of the lower member of the chassis of FIG. 2. A circuit board is shown mounted in the chassis.

The three-dimensionally spaced electronic components are interconnected with conductive cabling in the form of wires, busses, ribbon cable, and the like. As a means for cable management, pre-patterned cable channels are formed in the chassis to hold and guide the cables through pre-defined locations within the electronic device. For example, with reference to FIG. 7, cable channels 94, 96, 98, and 100 are formed in bottom outer surface 74 of chassis 60 to route cables from circuit board 58 to different locations in the electronic device. Some of the channels, such as channels 94 and 100, are fairly deep. The wire bundles, represented by bundle 101, are inserted down into these channels and held therein via friction from the natural compliance of the foam walls. It is common for the cables to be connected to circuit board 58, or an electronic component, via an edge connector. In FIG. 7, edge connectors 102 and 104 are shown. Cable channels 96 and 98 each include a retaining wall 106 and 108, respectively, which prevent the cable from dislodging from the edge connector. When right angle connectors are used, the retaining walls can prohibit connectors from coming loose during shock and vibration.

The cable channels are advantageous over prior art techniques of bundling the cables using clips or hooks. One advantage is that the formed chassis has the cable channels in the same location from part to part, making assembly more convenient. The pre-formed channels also provide uniformity in cable placement within the electronic device which reduces the variability of RFI emissions from one manufactured device to the next. Such channels further eliminate the use of clips, hooks, and the like, thereby reducing the overall component and assembly costs.

The electronic device of this invention has several benefits. One benefit is that the chassis is configured to accommodate electronic components that posses large size tolerance ranges. Another benefit is that the components are arranged compactly and efficiently within a three-dimensional space to permit reduction in the overall dimensions of the electronic device. Additionally, smaller components can be employed since special sized recesses are formed in the chassis to support the smaller components, rather than using larger components which assimilate more easily into metal framework structures. Another benefit is the cable management afforded by the repeatable, molded cable channels.

The electronic device of this invention has been described in the context of a heart defibrillator system. However, other example types of electronic devices according to this invention include computers, test and measuring devices, spectrum analyzers, multimeters, signal sources, entertainment electronics, household appliances, lightwave test equipment, and analytical chemistry equipment.

In compliance with the statute, the invention has been described in language more or less specific as to structure and method features. It is to be understood, however, that the invention is not limited to the specific features described, since the means herein disclosed comprise exemplary forms of putting the invention into effect. The invention is, therefore, claimed in any of its forms or modifications within the proper scope of the appended claims appropriately interpreted in accordance with the doctrine of equivalents and other applicable judicial doctrines.

I claim:

1. A chassis for a defibrillator system, comprising:

an upper member having opposing outer and inner surfaces, the inner surface of the upper member having a monitor recess aligned along a first longitudinal axis for receiving a portion of a CRT display monitor, the outer surface of the upper member having a capacitor recess aligned along a second longitudinal axis for receiving a capacitor, the first longitudinal axis being substantially perpendicular to the second longitudinal axis; and a lower member having an inner surface in juxtaposition with the inner surface of the upper member and an opposing outer surface, the inner surface of the lower member having a CRT support cavity for supporting the CRT display monitor and the outer surface of the lower member having a circuit board recess for holding a circuit board.

2. A chassis as recited in claim 1 wherein the upper member of the chassis is formed so that the capacitor recess in the outer surface is elevationally above the monitor recess in the inner surface.

3. A chassis as recited in claim 1, further comprising an orientation coupling assembly to orient and align the upper member and the lower member.

4. A chassis as recited in claim 1, further comprising at least one deformable rib provided in the monitor recess of the upper member to position and hold the CRT display monitor in the recess along the first longitudinal axis.

5. A chassis as recited in claim 1, further comprising at least one cable channel formed in the outer surface of the lower member adjacent to the circuit board recess to hold and guide a cable used to transfer signals to and from the circuit board.

6. A defibrillator system comprising a plurality of electronic components; and the chassis as recited in claim 1 to hold the electronic components.

7. A heart defibrillator comprising:

a plurality of electronic components comprising a display monitor, a capacitor assembly to hold an electrical charge for a heart defibrillating pulse, and a relay to isolate a human patient from generation of the heart defibrillating pulse;

a chassis formed of expanded polyproplylene and configured to hold the electronic components in a predefined three-dimensional arrangement wherein some of the electronic components overlap with others of the electronic components, the chassis having separating elements positioned between the electronic components to provide the appropriate spacing between overlapping components; and the chassis has a lower member and an upper member formed with a monitor recess for supporting the display monitor, the upper member supporting the capacitor elevationally above, and overlapping with, the display monitor.

8. A heart defibrillator comprising:

a plurality of electronic components comprising a display monitor, a capacitor assembly to hold an electrical charge for a heart defibrillating pulse, and a relay to isolate a human patient from generation of the heart defibrillating pulse;

a chassis formed of expanded polypropylene and configured to hold the electronic components in a predefined three-dimensional arrangement wherein some of the electronic components overlap with others of the electronic components;

the chassis having an upper member having opposing outer and inner surfaces, the inner surface of the upper member having a monitor recess aligned along a first longitudinal axis for receiving a portion of a display monitor, the outer surface of the upper member having a capacitor recess aligned along a second longitudinal axis for receiving the capacitor, the first longitudinal axis being substantially perpendicular to the second longitudinal axis; and the chassis further having a lower member with an inner surface in juxtaposition with the inner surface of the upper member and an opposing outer surface, the inner surface of the lower member having a support cavity for supporting the display monitor.

9. A heart defibrillator comprising:

a plurality of electronic components comprising a display monitor, a capacitor assembly to hold an electrical charge for a heart defibrillating pulse, and a relay to isolate a human patient from generation of the heart defibrillating pulse; the electronic components being connected to conductive cables; and a chassis formed of expanded polypropylene and configured to hold the electronic components in a predefined three-dimensional arrangement wherein some of the electronic components overlap with others of the electronic components; and the chassis including cable channels formed therein to hold and guide the cables through predefined locations within the defibrillator.

10. A heart defibrillator comprising:

a plurality of electronic components comprising a display monitor, a capacitor assembly to hold an electrical charge for a heart defibrillating pulse, and a relay to isolate a human patient from generation of the heart defibrillating pulse;

a chassis formed of expanded polypropylene and configured to hold the electronic components in a predefined three-dimensional arrangement wherein some of the electronic components overlap with others of the electronic components; and the chassis including deformable ribs that deform under pressure from the display monitor to orient and hold the display monitor in the chassis.

* * * * *